(12) United States Patent
Van Der Voort et al.

(10) Patent No.: US 7,761,129 B2
(45) Date of Patent: Jul. 20, 2010

(54) MEASUREMENT HEAD FOR NON-INVASIVE BLOOD ANALYSIS

(75) Inventors: Marjolein Van Der Voort, Valdenswaard (NL); Bernardus Leonardus Bakker, Nijmegen (NL); Gerald Lucassen, Eindhoven (NL); Hendrikus Antonius Cornelus Maria Compen, Budel (NL); Michael Cornelis Van Beek, Eindhoven (NL); Wouter Harry Jacinth Rensen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 494 days.

(21) Appl. No.: 11/568,743

(22) PCT Filed: May 3, 2005

(86) PCT No.: PCT/IB2005/051430

§ 371 (c)(1),
(2), (4) Date: Jul. 25, 2007

(87) PCT Pub. No.: WO2005/107579

PCT Pub. Date: Nov. 17, 2005

(65) Prior Publication Data

US 2008/0262324 A1    Oct. 23, 2008

(30) Foreign Application Priority Data

May 11, 2004    (EP) .................................. 04102023

(51) Int. Cl.
   *A61B 5/145*    (2006.01)
(52) U.S. Cl. ........................ 600/344; 600/473
(58) Field of Classification Search .................. 600/344, 600/310; 359/393
See application file for complete search history.

(56) References Cited

U.S. PATENT DOCUMENTS

| 4,920,386 | A | | 4/1990 | Tsuchiya et al. |
| 5,879,373 | A | * | 3/1999 | Roper et al. ................. 600/344 |
| 6,115,621 | A | * | 9/2000 | Chin ........................... 600/323 |
| 6,147,749 | A | * | 11/2000 | Kubo et al. ................... 356/39 |

(Continued)

FOREIGN PATENT DOCUMENTS

EP     0801297 A1    10/1997

(Continued)

OTHER PUBLICATIONS

ISR: PCT/IB05/051430.

(Continued)

*Primary Examiner*—Eric F Winakur
*Assistant Examiner*—Etsub D Berhanu

(57) ABSTRACT

A measurement head has an objective for imaging of a target area such as including a capillary vessel in the skin. The measurement head does not require a lateral shifting of the optical axis of the objective. Transverse relative movements between the objective and a capillary vessel in the skin are performed by mechanically shifting the skin with respect to the objective of the measurement head. Moreover, the measurement head is adapted to host one or more pressure sensors for measuring the contact pressure between the measurement head and the skin. Pressure information may be exploited in order to calibrate a spectroscopic analyzer, and/or to regulate the contact pressure within predefined margins specifying an optimum range of contact pressure for spectroscopic examination of capillary vessels.

18 Claims, 5 Drawing Sheets

U.S. PATENT DOCUMENTS

Figure 1:
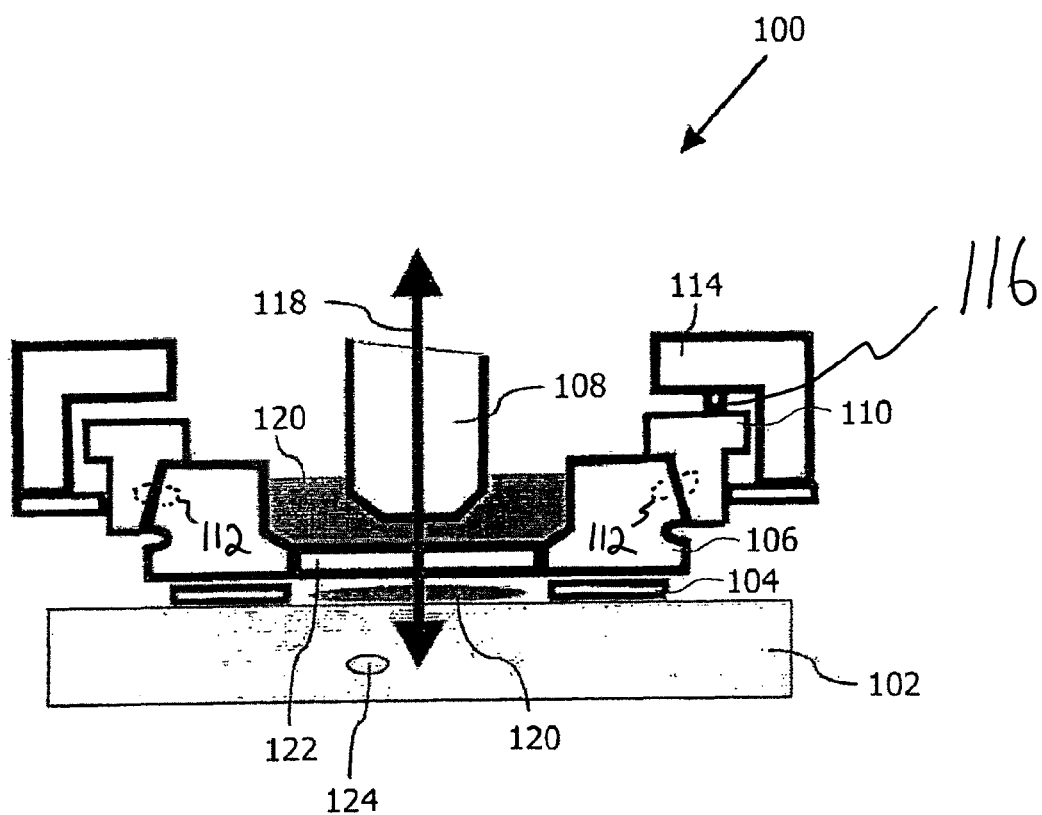

| | | |
|---|---|---|
| 6,345,191 B1 | 2/2002 | Hartmann et al. |
| 6,379,317 B1 * | 4/2002 | Kintzig et al. ............... 600/573 |
| 6,571,117 B1 | 5/2003 | Marbach |
| 2003/0032872 A1 * | 2/2003 | Rule et al. .................. 600/309 |

FOREIGN PATENT DOCUMENTS

| | | |
|---|---|---|
| WO | 9627325 | 9/1996 |
| WO | 0128418 A1 | 4/2001 |
| WO | 02057758 A1 | 7/2002 |
| WO | 02057759 A1 | 7/2002 |
| WO | 2005004712 A1 | 1/2005 |

OTHER PUBLICATIONS

Written Opinion: PCT/IB05/051430.

\* cited by examiner

MEASUREMENT HEAD FOR NON-INVASIVE BLOOD ANALYSIS

The present invention relates to the field of in vivo non-invasive blood analysis (NIBA) by making use of optical imaging and spectroscopic techniques.

Usage of optical spectroscopy techniques for analytical purposes is as such known from the prior art. WO 02/057758 A1 and WO 02/057759 A1 show spectroscopic analysis apparatuses for in vivo non-invasive spectroscopic analysis of the composition of blood flowing through a capillary vessel of a patient. The position of the capillary vessel is determined by an imaging system in order to identify a region of interest to which an excitation beam for the spectroscopic analysis has to be directed. Preferably, the imaging and the spectral analysis of the region of interest is performed simultaneously. In principle, any imaging method providing sufficient visualization of a capillary vessel can be applied. The imaging as well as the spectroscopic analysis both make use of a common microscope objective enabling imaging of a capillary vessel on the one hand and allowing focusing of a near infrared laser beam in the skin for exiting a Raman spectrum on the other hand. Moreover, the same microscope objective is used for collection of the scattered radiation evolving from the Raman processes.

Making use of a high-numerical-aperture objective, and a pinhole in front of the detector, Raman spectra can be taken from a small, confocal detection volume. However, capillary vessels in the skin being detected by the imaging system can either be located on the optical axis of the microscope objective or can be located off axis. In the latter case and due to the fact, that the confocal detection volume of the spectroscopic analysis system is rather small, the Raman detection volume has to be shifted into a selected volume of interest covering at least a part of a capillary vessel being typically located at a certain depth underneath the surface of the skin of the patient.

In principle various techniques can be applied in order to shift the Raman detection volume into a selected blood vessel. First, the angle of incidence between the objective and the laser beam exiting the Raman spectra can be changed, while keeping the objective and the skin fixed. Such an approach is advantageous with respect to its mechanical implementation but comes along with a complicated (and possibly expensive) optical design. Furthermore, when shifting the detection volume in this way, not only the excitation path is changed, but also the detection path needs to be adjusted. A second approach focuses on moving the objective with respect to the skin. Preferably, the optical axis of the objective, hence the objective itself, is subject to lateral translation, i.e. translation in a plane perpendicular to the optical axis. Furthermore in this approach, the objective is subject to a longitudinal translation, i.e. a movement along the optical axis of the objective. Such a solution allows to maintain the angle of incidence between the laser beams for spectral analysis and imaging and the objective. In this case, the spectroscopic detection volume is kept on the optical axis allowing for a less complicated optical design than the above-mentioned approach.

However, both approaches require some kind of design for shifting the confocal detection volume of the spectral analysis system in both lateral and longitudinal directions. Alternatively, the optical axis of the objective has to be moved in either direction transversal and longitudinal involving a transversal and longitudinal displacement of the microscope objective itself. It is clear, that both approaches involve a complicated optical design.

The present invention therefore aims to provide an alternative way to move the volume of interest into the detection volume of the spectroscopic system.

The present invention provides a measurement head for a spectroscopic system. The inventive measurement head comprises fixing means for fixing the measurement head to an area of the surface of the skin of a patient. Preferably, the inventive measurement head incorporates necessary optical components for imaging and spectroscopic analysis. Preferably, it features a compact design and its functionality is principally limited to expose an area of the skin to the appropriate radiation and to capture imaging signals and scattered spectroscopic signals. The necessary light sources as well as optical signal analysis means are provided by a base unit being connected with the measurement head.

The spectroscopic system is particularly designed for determining of a property of a fluid flowing through a biological tubular structure in a target area underneath the surface of the skin of a patient. The target area defines a volume of interest being imaged by an imaging system of the spectroscopic system for retrieving biological tubular structures such as capillary blood vessels. After determination of the position of a distinct capillary vessel, it is moved to the optical axis of the spectroscopic system allowing for a focusing of an excitation beam into the capillary vessel.

Moreover, the target area may also define an area of interest underneath the surface of the skin or even on the surface of the skin of the patient. This allows for universal spectroscopic analysis not only of e.g. blood vessels located underneath the surface of the skin but also a spectroscopic analysis of various biological structures like hairs or sweat glands, etc that are located on the surface of the skin.

The measurement head is especially designed for fixing to various parts of the skin of a patient that are easily accessible and/or provide a high density of capillary vessels being suitable for spectroscopic analysis. Once attached and fixed to the skin the measurement head remains in the fixed position in such a way that the optical axis and the confocal detection volume of the objective remain in a capillary vessel at least for the time needed for capturing the spectroscopic data which is in the range of a few seconds.

The functionality of the objective of the measurement head is twofold. First, it provides a focusing of the spectra excitation laser beam and collection of the resulting scattered radiation. Second, it has the functionality of imaging of an area of the skin being substantially larger than the confocal detection area of the spectroscopic beam.

Suitable imaging methods include Orthogonal Polarized Spectral Imaging (OPSI), Confocal Video Microscopy (CVM), Optical Coherence Tomography (OCT), Confocal Laser Scanning Microscopy (CLSM) and Doppler Based Imaging. Corresponding imaging techniques are disclosed in U.S. 60/262,582, EP02732161.1, IB2004/050251 und EP03102481.3, the entirety of which is herein incorporated by reference. Moreover, alternative imaging techniques based on ultrasound or ultrasound in combination with a contrast agent are also applicable.

According to a further preferred embodiment of the invention, the measurement head further comprises means for moving the fixing means relative to the objective in a plane substantially perpendicular to the optical axis of the objective for moving the volume of interest into the optical axis of the objective. Since the fixing means of the measurement head being adapted to be rigidly fixed to the surface of the skin of a patient, by moving the fixing means relative to the objective, an area of the surface of the skin of the patient is substantially moved with respect to the objective. In this way, a capillary vessel being imaged by the imaging system and lying off axis with respect to the optical axis of the objective can be translated to the optical axis of the objective into a region substantially overlapping with the confocal detection volume of the measurement head.

In other words, fixing the fixing means of the measurement head to an area of the surface of the skin of the patient and moving the fixing means, i.e. moving the skin with respect to the objective of the measurement head provides a required translational movement of the skin with respect to the objective. The invention therefore provides an efficient, compact and robust approach for positioning a target area in such a way, that it substantially overlaps with a distinct capillary vessel. In contrast to solutions known in the prior art, the invention provides a movement of the skin with respect to the objective. This allows for a less complicated optical design, because the lateral position of the optical axis of the objective does not have to be modified. Moreover, the inventive measurement head does not require any means for shifting the optical axis of the objective.

It is of advantage that the measurement head features a compact design in such a way, that the measurement head can be easily attached and fixed to a designated portion of the skin of the patient. When the measurement head is sufficiently small in size and weight, the constraints regarding the freedom of movement of the patient are kept at a low level, because the measurement head is free to follow almost any conceivable movement of the patient. Allowing the patient to move during examination is certainly more comfortable than remaining rigidly fixated in a somewhat uncomfortable position during examination.

According to a further preferred embodiment of the invention, the inventive measurement head further comprises means for moving the objective relative to the fixing means in a direction substantially parallel to the optical axis of the objective for moving the focal plane of the objective into the target area underneath the surface of the skin. In this way, the longitudinal position of the confocal detection volume can be arbitrarily modified, providing a three dimensional relative movement between the objective of the measurement head and a capillary vessel being subject to investigations and being located underneath the surface of the skin.

Hence, the invention provides a lateral movement of a capillary vessel or other biological structures located on the surface of the skin with respect to the objective by moving the skin with respect to the objective and further provides a longitudinal movement of the objective with respect to the capillary vessel. Since the optical arrangement of the measurement head makes use of an infinity corrected objective for the imaging as well as confocal spectroscopic means, a translation of the objective in the direction of the optical axis can easily be realized without implementation of optical correction means, correcting a longitudinal translation of the objective.

Any type of translation of the measurement head, either of lateral or longitudinal type, can in principle be realized by any kind of translation stages, combinations of translating and rotating stages that can either be driven electrically, magnetically or pneumatically.

According to a further preferred embodiment of the invention, the fixing means comprise an adhesive element being adapted to be in contact with the area of the surface of the skin. The adhesive element is adapted to prevent a relative movement between the area of the surface of the skin and the fixing means of the measurement head. In other words, the measurement head is fixed to the surface of the skin by sticking the fixing means of the measurement head to the surface of the skin. Making use of adhesive fixing of the measurement head to the surface of the skin is preferably applicable when the skin is relatively dry, i.e. not covered by e.g. saliva.

Making use of applying adhesive elements on dry regions of skin, in most cases it might be sufficient to slightly press the fixing means of the measurement head into the skin in order to appropriately attach an area of the surface of the skin to the fixing means. A lateral translation of the fixing means with respect to the objective then results in a corresponding lateral movement of the area of the surface of the skin. In particular, by making use of a material featuring a high frictional force between the surface of the skin and the material, such as e.g. rubber, or by making use of surface-roughened material, allows to decrease the required contact pressure. When required, even a firm attachment of the fixing means can be realized by making use of double sided sticky material or glue.

According to a further preferred embodiment of the invention, the fixing means further comprise a first and a second clamping element. The first clamping element being an integral part of a housing of the measurement head and the first and the second clamping elements being adapted to exert mechanical stress to the surface of the skin. Thus, the first and the second clamping element form a type of clamp being particularly applicable to those parts of the skin of the body that can be easily folded or regions of the skin of a patient that allow for clamping due to their geometry. Parts of the skin that can be easily folded are for example the back of the upper arm or some parts of the face. Parts of a body allowing for clamping by virtue of their geometry are for example: ear lobes, lips, tongue, nostrils, or skin flaps between fingers. In this way, also inner parts of a body that are accessible from outside can be sufficiently examined.

According to a further preferred embodiment of the invention, the fixing means comprise at least a first and a second magnetic element. The first and the second magnetic element being arranged to mutually exert an attractive magnetic force. The first magnetic element being an integral part of the housing of the measurement head and the second magnetic element being adapted to be separated apart from the first magnetic element by a volume of the tissue of the patient containing the volume of interest underneath the skin. In this way, the measurement head can be attached and fixed to the skin of the patient by making use of two mutually attracting magnetic elements. Such an embodiment is particularly applicable for regions of the body that can be reached from two sides but do not allow for sticking or clamping as for example the inside cheeks.

According to a further preferred embodiment of the invention, the fixing means further comprise means for generating a first barometric pressure between the area of the surface of the skin and the fixing means. Here, this first barometric pressure being substantially smaller than the surrounding barometric pressure leading to an efficient attachment of the measurement head to the surface of the skin. In this embodiment, the fixing means preferably make use of a chamber being adapted to be in contact with the skin and having small holes. After getting in contact with the surface of the skin, the chamber becomes subject to a vacuum. Consequently, near the holes of the chamber, the negative pressure exerts an attractive force to the surface of the skin resulting in a fixing of the chamber and consequently a fixing of the fixing means of the measurement head to the skin of the patient.

According to a further preferred embodiment of the invention, the fixing means comprise at least one disposable element being adapted to be in contact with the surface of the skin. In this way, special care can be taken with respect to hygiene. Preferably, only those parts of the fixing means being adapted to be in mechanical contact with the skin of the patient are designed as disposable elements. Alternatively, when the fixing means or parts of the fixing means are designed as an integral part of the housing of the measurement head, the fixing means in its entirety can be designed as a disposable. In principle any of the above mentioned embodiments for fixing of the measurement head to the surface of the skin can be designed and manufactured as a disposable element.

According to a further preferred embodiment of the invention, the fixing means being rigidly connected to the objective and the measurement head further comprises at least a first and a second displacing element being adapted to be in contact with the surface of the skin. The first displacing element being adapted to displace an area of the surface of the skin along a first direction and the second displacing element being adapted to move the area of the surface of the skin along a second direction. Both the first and the second directions being substantially perpendicular to the optical axis of the objective.

Furthermore, the first direction is substantially perpendicular to the second direction. In this embodiment, the fixing means of the measurement head are adapted to be laterally shifted with respect to the optical axis of the objective. In particular, this embodiment makes use of the flexible properties of the skin and applies at least two displacing elements for laterally displacing an area of the surface of the skin with respect to the fixing means and the objective of the measurement head. For example, the displacing elements can be accomplished as caterpillar like wheels finished with rubber pads. By rotating the wheels, the skin can be sufficiently pulled into a desired lateral direction.

According to a further preferred embodiment of the invention, the fixing means of the measurement head further comprise a window being an integral part of the housing of the measurement head. The window being substantially transparent for the type of optical radiation being applied for imaging and spectroscopic analysis of the skin and the confocal detection volume.

According to another embodiment of the invention, the measurement head has at least one pressure sensor measuring a contact pressure between the measurement head and the surface of the skin. Preferably, the at least one pressure sensor is integrated into the fixing means, or between a disposable and a non-disposable part of the measurement head. Measuring a contact pressure and providing the measured contact pressure to an analysis system eventually allows to modify the contact pressure. Knowledge of the contact pressure may be an important parameter to appropriately calibrate the spectroscopic analysis system. Furthermore, it might be necessary to modify the contact pressure that may have to be within a certain range, otherwise discarding the measured results.

In principle, the inventive fixing mechanisms allows a modification of the contact pressure. Making use of the vacuum technique, the contact pressure can easily by modified by altering the power of a connected vacuum pump. Making use of a clamping mechanism, it is generally possible to implement the clamping spring as a temperature sensitive alloy, being subject to deformation when applied with an electric current. Also by making use of the magnetic fixing approach, it is generally possible to modify the magnetic force by applying electromagnets in combination with a modifiable voltage.

In another aspect, the invention provides fixing means for fixing of a measurement head to an area of the surface of the skin of a patient. The fixing means being adapted to prevent a lateral movement of an area of the surface of the skin of a patient during an examination period. Furthermore, the fixing means being adapted to be laterally moved with respect to the objective in order to bring the lateral position of the confocal detection volume to a distinct capillary vessel beneath the surface of the skin. Moreover, the fixing means being adapted to keep a distinct capillary vessel being subject to examination on the optical axis of the objective of the measurement head.

According to a further preferred embodiment of the invention, the fixing means being adapted for fixing the housing of the measurement head to the area of the surface of the skin. In this way the measurement head can be rigidly or firmly attached to a designated area of the surface of the skin. In combination with means for moving the fixing means or with displacing means, an area of the surface of the skin can be laterally shifted with respect to the objective of the measurement head.

According to a further preferred embodiment of the invention, the fixing means comprise at least one disposable element being adapted to be in contact with the surface of the skin. Making use of disposable elements provides a high level of hygienic standard providing an easy and universal adaptation of the measurement head to a variety of different bodies being subject to examination.

In still another embodiment the invention provides a method for positioning of a measurement head of a spectroscopic system with respect to a target area. The method for positioning the measurement head makes use of applying a fixing means of the measurement head to an area of the surface of the skin, and moving of the fixing means of the measurement head with respect to an objective of the measurement head for imaging of the target area and for positioning the target area on the optical axis of the objective. The target area specifies a biological tubular structure in a volume of interest underneath the surface of the skin or other biological structures located on or underneath the surface of the skin. Positioning of the target area on the optical axis of the objective allows for confocal spectroscopic analysis of the target area by making use of the same objective.

It is to be noted, that the present invention is not restricted to a particular type of Raman spectroscopy but that other optical spectroscopic techniques can also be used. This includes (i) other methods based on Raman scattering including stimulated Raman spectroscopy and coherent anti-Stokes Raman spectroscopy (CARS), (ii) infra-red spectroscopy, in particular infra-red absorption spectroscopy, Fourier transform infra-red (FTIR) spectroscopy and near infra-red (NIR) diffusive reflection spectroscopy, (iii) other scattering spectroscopy techniques, in particular fluorescence spectroscopy, multi-photon fluorescence spectroscopy and reflectance spectroscopy, and (iv) other spectroscopic techniques such as photo-acoustic spectroscopy, polarimetry and pump-probe spectroscopy. Preferred spectroscopic techniques for application to the present invention are Raman spectroscopy and fluorescence spectroscopy.

Figure 2:
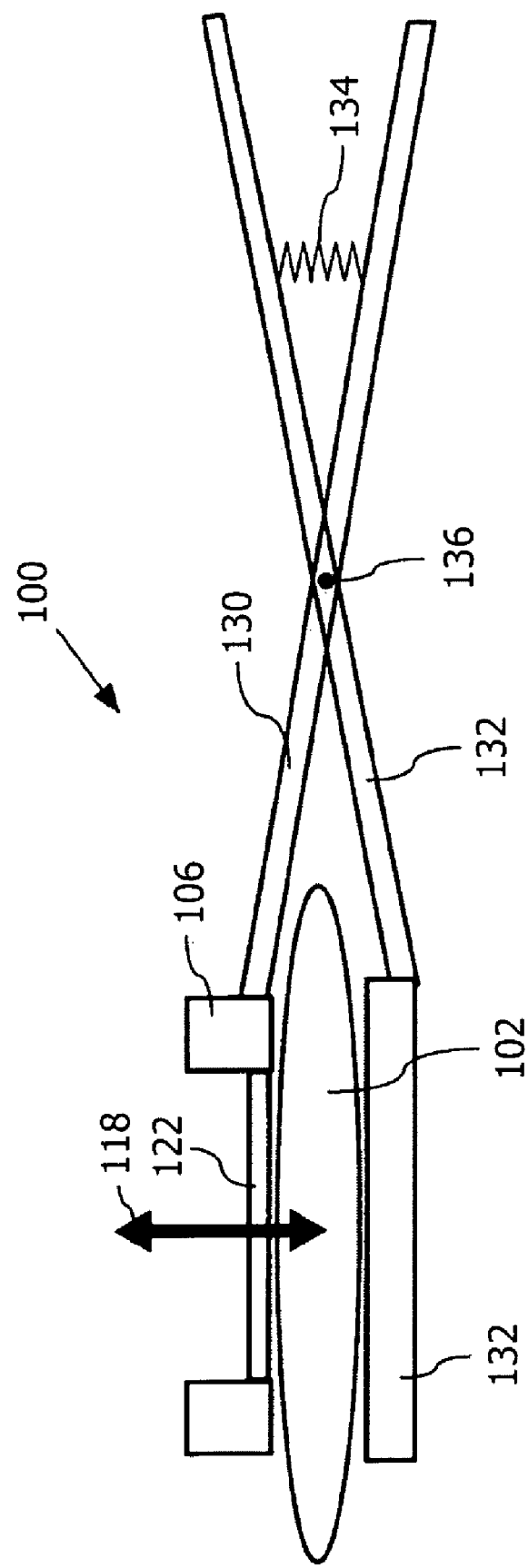
Figure 3:
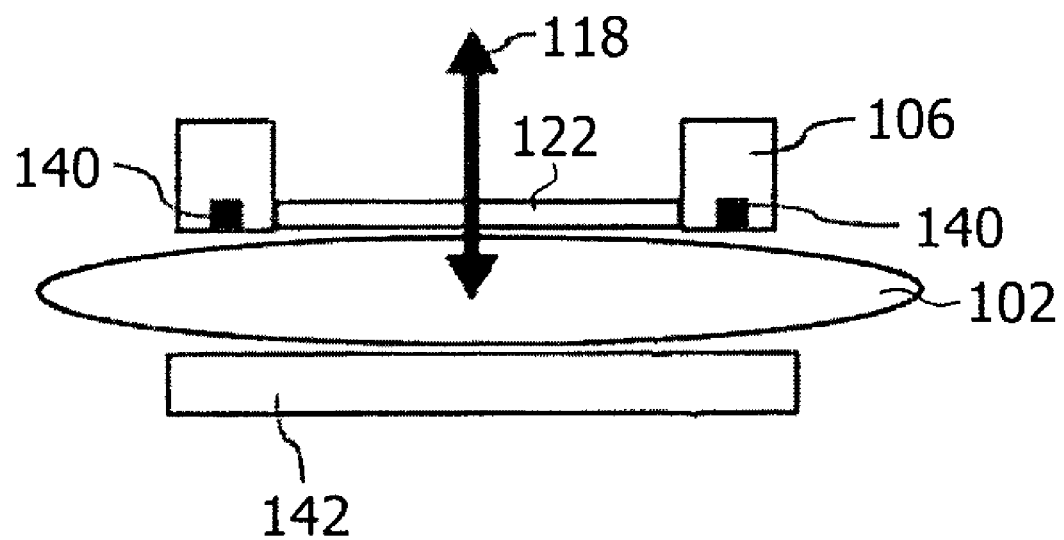
Figure 3:
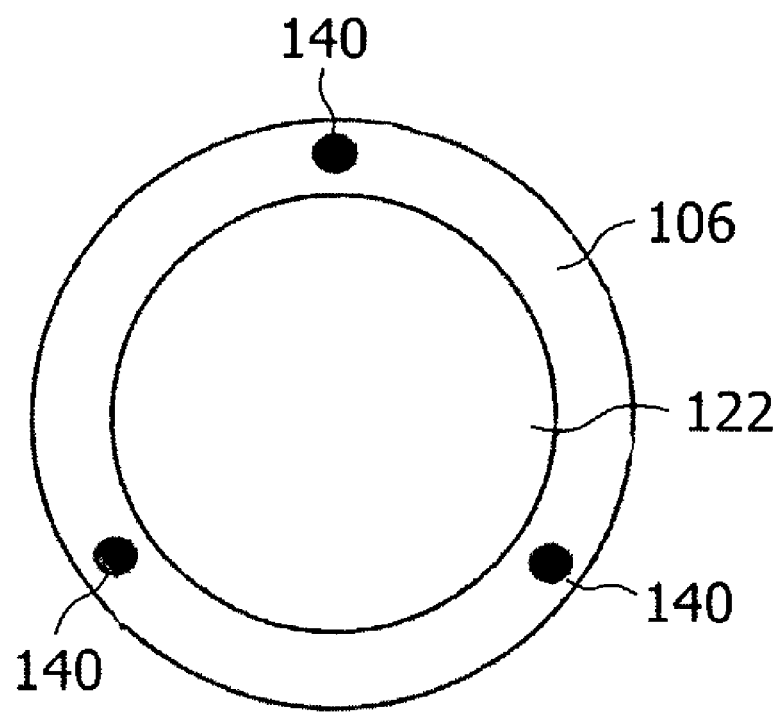
Figure 4:
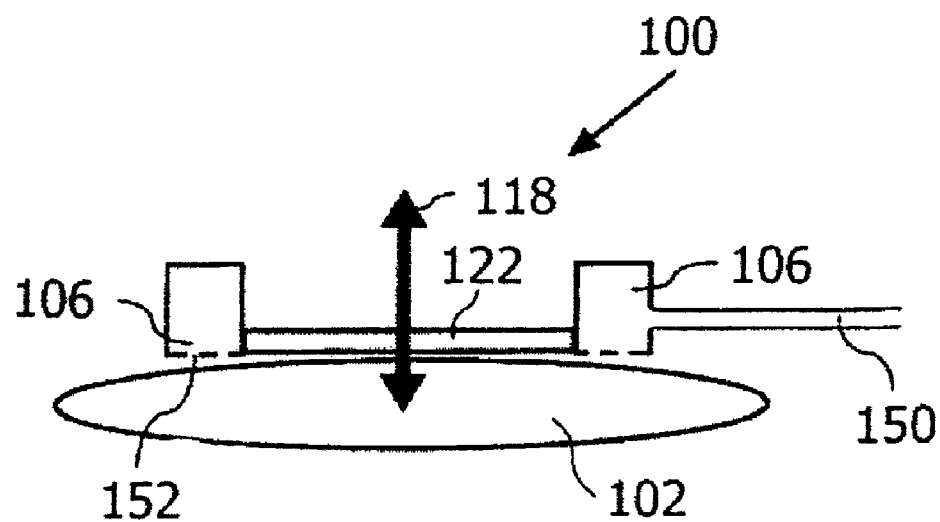
Figure 4:
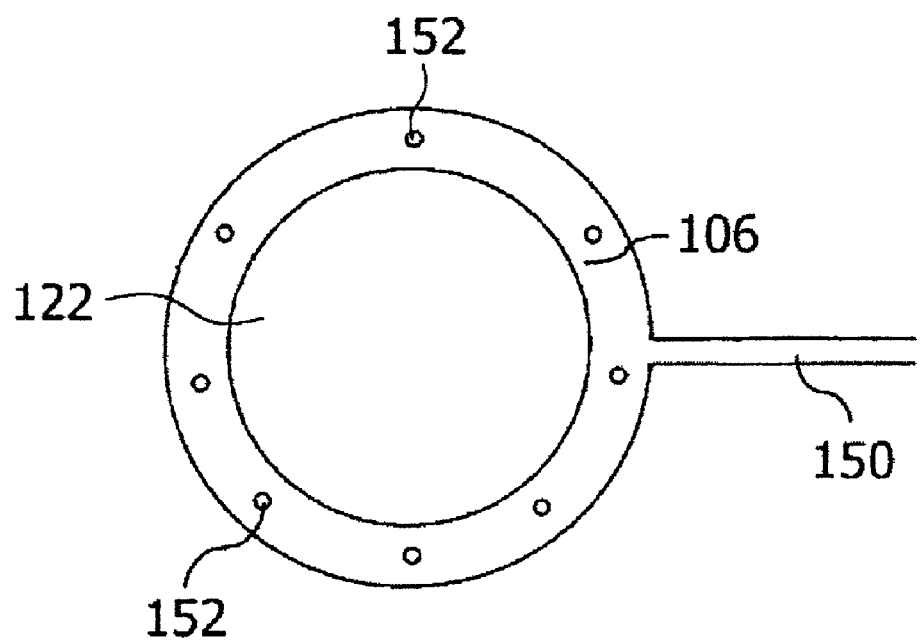
Figure 5:
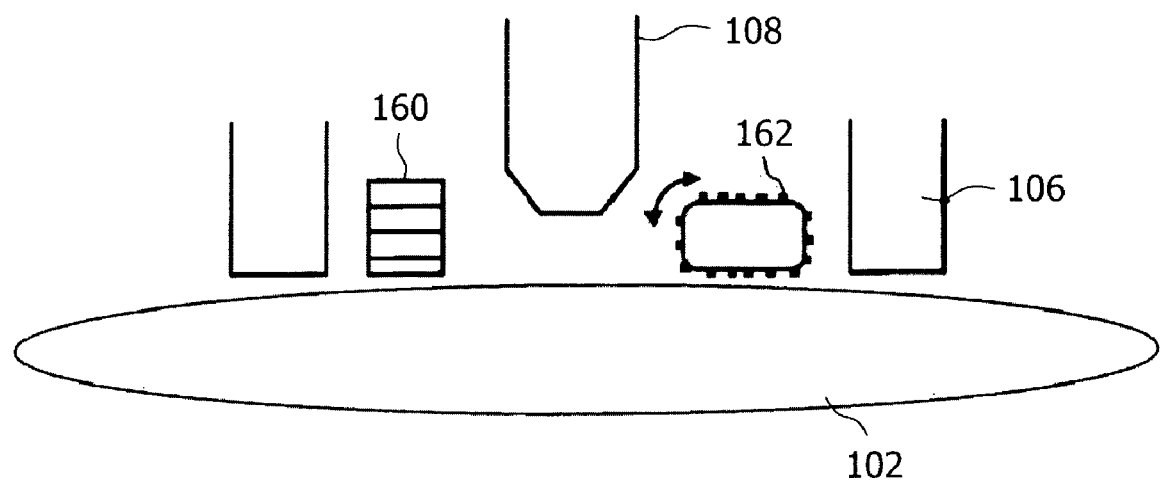
Figure 5:
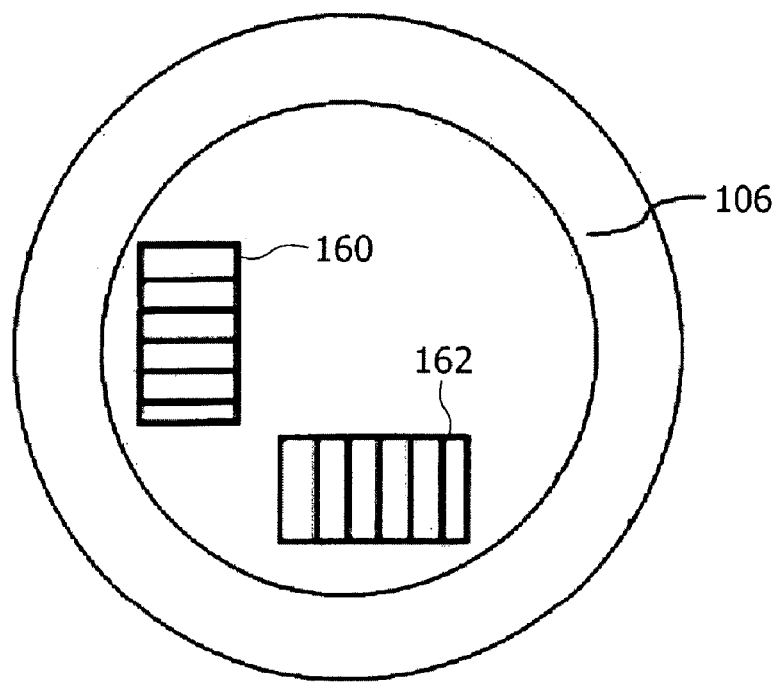

In the following preferred embodiments of the invention will be described in greater detail by making reference to the drawings in which:

FIG. 1 shows a cross sectional illustration of the measurement head being attached to the skin, FIG. 2 shows a cross sectional illustration of the measurement head making use of first and second clamping elements as fixing means, FIG. 3 shows a cross sectional and a top view illustration of the measurement head making use of attractive magnetic forces as fixing means, FIG. 4 shows a cross sectional illustration of the measurement head making use of a vacuum technique for fixing the measurement head to the skin, FIG. 5 depicts a cross sectional illustration and a top view of an embodiment of the measurement head making use of two displacing elements.

FIG. 1 shows a cross sectional illustration of the measurement head 100. The measurement head 100 being fixed to an area of the surface of a skin 102 by making use of fixing means 104. In this illustrated embodiment, the fixing means 104 are accomplished as adhesive strips sticking to a ring 106 of the measurement head 100 and to the surface of the skin 102. The ring 106 has a window 122 and can be filled with an immersion liquid 120. For reasons of imaging quality a droplet of immersion liquid 120 is also put between the window 122 of the measurement head 100 and the surface of the skin 102. In this way optical signals 118 used for imaging of the skin as well for spectroscopic examination of the skin solely propagate through media substantially featuring a similar refractive index.

For both imaging of the skin 102 as well as spectroscopic examination of a particular capillary vessel 124 beneath the surface of the skin, the objective 108 is used. The position of the objective 108 defines the position of the confocal detection volume for the spectroscopic analysis of the fluid flowing in the capillary vessels. By means of the imaging system also making use of the objective 108, a capillary vessel 124 can be identified eventually requiring a relative movement between the capillary vessel, i.e. an area of the skin, and the objective 108.

Therefore, the objective being adapted to be movable in longitudinal direction, i.e. in the direction parallel to the optical axis of the objective 108. Moving of the objective 108 can in principle be realized by any kind of translation stages making use of e.g. piezo-electric elements, magnetic elements or pneumatic elements. The optical arrangement for confocal excitation and capturing of scattered spectroscopic signals has been designed such, that a longitudinal shifting of the objective 108 in principle does not require any optical correction means. Hence, the measurement head can be designed without any optical correction means allowing for an efficient, compact and robust design of the measurement head.

Making efficient use of the inventive feature of laterally moving the skin 102 with respect to the objective 108 of the measurement head 100 allows for a rigid connection of the objective and the frame 114 of the measurement head in such a way, that the objective 108 is solely moveable along its optical axis with respect to the frame 114. A lateral movement, i.e. a movement in the plane perpendicular to the optical axis of the objective 108 can be performed by means of the translation stages being an integrated part of the frame 114 and the ring 110. These translation stages allow for a relative lateral translation of the ring 110 with respect to the frame 114. The translation stages provide a lateral movement in both lateral directions, i.e. in the two directions being substantially perpendicular to the optical axis of the objective 108. Preferably, the measurement head 100 has a couple of translation stages being located at different positions of the frame 114 or the ring 110 in such a way that the two rings 110 and 106 can be translated in both directions of the lateral plane with respect to the frame 114 and the objective 108.

The ring 110 serves as a holder of the ring 106. The ring 106 serving as a cup for the immersion liquid is preferably attached to the ring 110 by magnetic means in combination with an arrangement of springs 112 providing for a horizontal orientation of the ring 106, i.e. guaranteeing that the ring 106 and its integrated window 122 remain in an orientation being substantially perpendicular to the optical axis of the objective 108.

Ideally, the measurement head is adapted to host at least one pressure sensor in order to measure and to provide a contact pressure between the surface of the skin and the measurement head. Having knowledge of the contact pressure may further be exploited in order to calibrate the spectroscopic analysis system and/or to adjust the contact pressure lying within a predefined optimum range.

In order to provide a high level of hygienic standard, at least the fixing means 104 in form of adhesive strips in this embodiment have been preferably implemented as disposable. Alternatively, when the fixing means 104 are rigidly connected to the ring 106, the entire ring 106 and the window 122 as well as the immersion liquid 120 being integral parts of the ring 106 can be implemented as a disposable element.

The embodiment illustrated in FIG. 1 is particularly applicable to areas of the skin that allow for a sufficient adhesion between the fixing means 104 of the measurement head 100 and the surface of the skin 102.

FIG. 2 shows a cross sectional illustration of the measurement head 100 in an embodiment making use of at least two clamping elements 130 and 132. Here, for reasons of simplicity only the ring 106 and the window 122 of the measurement head of FIG. 1 are illustrated. The ring 106 being connected with the first clamp element that is connected to a second clamp element 132 by means of a common axis. Both clamp elements 130, 132 are free to rotate around the common axis 136. The lower left part of the clamp element 132 has a geometric shape similar to the ring 106 of the measurement head 100. The first and the second clamp element 130 and 132 are adapted to clamp a particular part of the skin 102. Suitable parts of the skin 102 that allow for clamping are for example ear lobes, lips, tongue, nostrils, skins flaps between fingers or any other part of the skin that can be easily folded for example the back of the upper arm or some parts of the face.

The strength of the clamping effect is governed by an actuator 134 being connected with both clamp elements 130, 132 and exerting an attractive force on both clamping elements 130, 132. By application of an attractive force between the two clamping elements 130, 132 mechanical stress is exerted on the piece of skin 102 resulting in a fixing of the skin 102 with respect to the ring 106 of the measurement head 100.

Making use of pressure sensors being incorporated in the measurement head 100 providing a contact pressure between the measurement head and the surface of the skin allows to modify the attractive force exerted between the two clamping elements 130, 132 in order to realize a predetermined value of contact pressure. Manipulation of the spring force can in principle be realized by a variety of different means, such as e.g. manufacturing the spring by making use of a distinct temperature sensitive alloy in combination with a heating unit.

FIG. 3 shows a cross sectional and a top view of an embodiment of the measurement head 100 wherein the fixing means being adapted to make use of a magnetic effect. Similar as depicted in FIG. 2 only the ring 106 and the incorporated window 122 of the measurement head 100 are illustrated here. The ring 106 has a couple of magnets 140 being preferably arranged in a regular order around the ring 106. In this way, the ring 106 serves as one element of the fixing means for fixing the measurement head to a particular part of the skin 102. The second part of the fixing means is provided by a magnetic disk 142 serving as a counterpart for the magnets 140 of the ring 106. The magnets 140 of the ring 106 and the magnetic disk 142 mutually exert an attractive force resulting in a fixing of the skin 102 relative to the ring 106 of the measurement head 100.

Making use of this embodiment is particularly advantageous to those parts of a body where neither clamping nor sticking is advisable, for example the inner cheeks. Also here, by making use of pressure sensors and implementing the magnets 140 as electro-magnets, allows for a universal adaptation and regulation of the contact pressure between the ring 106 and the skin 102. Also here with respect to hygienic aspects, the entire ring 106, window 122 and disk 142 can be designed as a disposable element.

FIG. 4 depicts a cross sectional and a top view of a further embodiment of the measurement head 100, wherein the fixing means being adapted to make use of a vacuum effect. In this embodiment, the ring 106 has a number of holes 152 that are adapted to be in contact with the skin 102. In particular, the ring 106 is implemented as a vacuum chamber and being therefore connected to a tube. Bringing the ring 106 in contact with the skin 102 and connecting the tube 150 to a kind of vacuum pump generating a vacuum inside the ring 106. Making use of a barometric pressure inside the ring 106 being lower than the surrounding barometric pressure allows to fixate the skin 102 to the ring 106 and thus fixing the measurement head to the skin.

This embodiment making use of the vacuum technique is similarly applicable to parts of the skin being accessible only from one side as the embodiment making use of adhesive elements as depicted in FIG. 1. Manipulating the vacuum inside the chamber 106 by appropriate controlling of the vacuum mechanism being attached to the tube 150 allows to modify the contact pressure between the ring 106 and the skin 102. Hence, the contact pressure can be arbitrarily modified in order to realize a predetermined contact pressure being advantageous for the spectroscopic examination of the capillary vessel 124.

FIG. 5 depicts a cross sectional and a top view illustration of another embodiment making use of two displacing elements 160 and 162. The two displacing elements are implemented as wheels, e.g. caterpillar like wheels, finished with rubber pads. The displacing elements get in contact with the skin 102 and due to a relatively high frictional force between the rubber pads of the displacing elements and the skin 102, rotating of the caterpillar like wheels results into a corresponding shifting of the skin 102 with respect to the objective 108 and with respect to the ring 106.

In general, any one or any combinations of the aforementioned fixing techniques can be applied here. In particular the fixing means do not have to be laterally shifted with respect to the objective 108. This embodiment efficiently makes use of the elastic properties of the surface of the skin 102. Referring to the top view illustration of the ring 106 and the two displacing elements 160 and 162, it is obvious that a rotation of the caterpillar like wheel 160 results in a vertical movement of the underlying skin and that a rotation of the caterpillar like wheel 162 results in a horizontal shift of the skin 102. The arrow in the upper illustration indicates the sense of rotation of the caterpillar like wheel finished with the rubber pads.

The present invention provides an efficient approach of attaching and fixing a measurement head for a spectroscopic system to a variety of different parts of the skin of a patient. The measurement head preferably features a compact design providing a flexible handling and offering a huge variety of application areas taking into account the plurality of properties of various portions of the skin. Furthermore, the measurement head features a robust and uncomplicated optical design not requiring a lateral shifting of the optical axis of the objective. Such transverse relative movements between the objective and a capillary vessel in the skin are preferably performed by mechanically shifting the skin with respect to the objective of the measurement head. Moreover, the measurement head is adapted to host a plurality of pressure sensors measuring the contact pressure between the measurement head and the skin. This pressure information can further be exploited in order to calibrate the spectroscopic analysis means, to regulate the contact pressure within predefined margins specifying an optimum range of contact pressure for spectroscopic examination of capillary vessels.

LIST OF REFERENCE NUMERALS 100 measurement head
102 skin
104 fixing means
106 ring
108 objective
110 ring
114 frame
118 optical signal
120 immersion liquid
122 window
124 capillary vessel
130 clamp element
132 clamp element
134 actuator
136 axis
140 magnet
142 magnetic disk
150 tube
152 hole
160 displacing element
162 displacing element

The invention claimed is:

1. A measurement head for a spectroscopic system comprising:
    fixing means for fixing the measurement head to an area of the surface of the skin of a patient, wherein the fixing means are configured to remain fixed to the area of the surface of the skin;
    an objective for imaging of a target area located below the surface of the skin, for directing an excitation beam to the target area, and for collecting return radiation from the target area; and
    lateral moving means for moving the fixing means in a plane substantially perpendicular to an optical axis of the objective.

2. The measurement head according to claim 1, further comprising means for moving the objective relative to the fixing means in a direction substantially parallel to the optical axis of the objective for moving the focal plane of the objective to the target area.

3. The measurement head according to claim 1, wherein the fixing means comprises an adhesive element being adapted to be in contact with the area of the surface of the skin, the adhesive element being further adapted to prevent a relative movement between the area of the surface of the skin and the fixing means.

4. The measurement head according to claim 1, wherein the fixing means comprises a first clamping element and a second clamping element, the first clamping element being an integral part of a housing of the measurement head, the first and the second clamping elements being adapted to exert mechanical stress to the surface of the skin, the first clamping element being configured to move the area of the surface of the skin in a first direction and the second clamping element being configured to move the area of the surface of the skin in a second direction which is opposite the first direction, the first direction and the second direction being perpendicular to the optical axis.

5. The measurement head according to claim 1, wherein the fixing means comprises at least a first and a second magnetic element, the first and the second magnetic element mutually exerting an attractive magnetic force, the first magnetic element being an integral part of a housing of the measurement head and the second magnetic element being adapted to be spaced apart from the first magnetic element by a volume of the tissue of the patient containing the target area.

6. The measurement head according to claim 1, wherein the fixing means comprises means for generating a first barometric pressure between the surface of the skin and the fixing means, the first barometric pressure being substantially smaller than the surrounding barometric pressure.

7. The measurement head according to claim 1, wherein the fixing means comprises at least one disposable element, the at least one disposable element being adapted to be in contact with the area of the surface of the skin.

8. The measurement head according to claim 1, wherein the fixing means is rigidly connected to the objective, the measurement head further comprising at least a first and a second displacing element being adapted to be in contact with the area of the surface of the skin, the first displacing element being adapted to displace the area of the surface of the skin along a first direction and the second displacing element being adapted to move the area of the surface of the skin along a second direction, the first and the second direction being substantially perpendicular to the optical axis of the objective, the first direction being substantially perpendicular to the second direction.

9. The measurement head according to claim 1, wherein the fixing means comprises a window, the window being an integrated part of a housing of the measurement head.

10. The measurement head according to claim 1, further comprising at least one pressure sensor, the at least one pressure sensor measuring a contact pressure between the measurement head and the surface of the skin.

11. The measurement head according to claim 1, wherein the fixing means comprises a clamping spring for changing a contact pressure between the measurement head and the surface of the skin.

12. The measurement head according to claim 11, wherein the clamping spring comprises a temperature sensitive material subject to deformation in response to an electric current.

13. The measurement head according to claim 1, wherein the fixing means comprises electromagnetic clamps configured for producing variable magnetic force in response to a variable voltage.

14. The measurement head according to claim 1, wherein the fixing means comprises a vacuum chamber, a contact pressure between the measurement head and the surface of the skin being changeable by changing a pressure in the vacuum chamber.

15. The measurement head according to claim 1, wherein the fixing means comprises a ring having a window filled with an immersion liquid on a side of the objective, and wherein a drop of the immersion liquid is provided between the window and the surface of the skin.

16. The measurement head according to claim 15, further comprising a further ring and a spring; the further ring being configured to hold the ring, and the spring being configured to provide a horizontal orientation of the ring so that the ring and the window remain in an orientation being substantially perpendicular to the optical axis of the objective.

17. The measurement head according to claim 15, further comprising wheels having pads that provide friction between the pads and the skin, for moving the area of the surface of the skin in a parallel direction and a perpendicular direction to the optical axis.

18. A method for positioning of a measurement head of a spectroscopic system with respect to a target area located below a surface of a skin, the method of positioning comprising the acts of:

applying a fixing device of the measurement head to an area of the surface of the skin, moving the fixing device in a plane substantially perpendicular to an optical axis of an objective of the measurement head, and relative thereto, for imaging of the target area so that the area of the surface of the skin fixed to the fixing device is moved to the target area until the optical axis of the objective is located over the target area.

* * * * *